(12) United States Patent
Mafra-Neto

(10) Patent No.: US 7,887,828 B2
(45) Date of Patent: Feb. 15, 2011

(54) DUAL ACTION ORGANIC FORMULATION TO CONTROL TWO STAGES OF INSECT PESTS

(75) Inventor: Agenor Mafra-Neto, Riverside, CA (US)

(73) Assignee: ISCA Technologies, Inc., Riverside, CA (US)

( * ) Notice: Subject to any disclaimer, the term of this patent is extended or adjusted under 35 U.S.C. 154(b) by 687 days.

(21) Appl. No.: 11/982,946

(22) Filed: Nov. 6, 2007

(65) Prior Publication Data

US 2008/0254083 A1    Oct. 16, 2008

Related U.S. Application Data

(60) Provisional application No. 60/857,749, filed on Nov. 7, 2006.

(51) Int. Cl.
  *A01N 25/28*    (2006.01)
  *A01N 25/02*    (2006.01)
  *A01N 43/22*    (2006.01)

(52) U.S. Cl. .................. 424/409; 424/84; 424/405; 424/406; 424/407; 424/408; 424/417; 424/420; 514/28; 514/29

(58) Field of Classification Search .............. None
See application file for complete search history.

(56) References Cited

U.S. PATENT DOCUMENTS

| | | | |
|---|---|---|---|
| 5,290,556 | A | 3/1994 | McKibben et al. |
| 5,707,638 | A | 1/1998 | Losel et al. |
| 5,759,561 | A | 6/1998 | Angst et al. |
| 5,925,367 | A | 7/1999 | Angst et al. |
| 6,001,346 | A | 12/1999 | Delwiche et al. |
| 6,316,017 | B1 | 11/2001 | McKibben et al. |
| 6,793,937 | B2 * | 9/2004 | Quong ................ 424/489 |
| 2004/0208953 | A1 | 10/2004 | Heath |

FOREIGN PATENT DOCUMENTS

| | | |
|---|---|---|
| WO | 01/50857 A2 | 7/2001 |
| WO | WO 2008/057547 | * 11/2007 |

OTHER PUBLICATIONS

PCT International Search Report and Written Opinion of the International Searching Authority for: PCT/US07/23409, Sep. 24, 2008, 8 pages.

Lorusso, Patrizia, Examiner. Application No.: EP 07 86 7376, Supplementary European Search Report and Written Opinion, dated Jul. 26, 2010, Place of Search Munich. 11 pages.

Darriet Frederic et al. "Spinosad: A New larvicide against insecticide-resistant mosquito larvae". Database Biosis [Online] Biosciences Information Service XP002592258, *Abstract*, Journal of the American Mosquito Control Association, vol. 21, No. 4, Dec. 2005, pp. 495-496, ISSN: 8756-971X, 2 pages.

* cited by examiner

*Primary Examiner* — Neil Levy
(74) *Attorney, Agent, or Firm* — Stetina Brunda Garred & Brucker

(57) ABSTRACT

The present invention discloses systems and methods for controlling arthropod populations. The systems include a polymeric substrate, a semiochemical that is reactive upon an adult-stage arthropod, and an insecticide that is toxic to an immature-stage arthropod. The semiochemical may be a sex pheromone that disrupts mating behavior of the adult-stage arthropod. The insecticide may be a per os insecticide that only affects the immature-stage arthropod. The arthropod to be controlled may be gypsy moths, in which case the semiochemical may be disparlure and the insecticide may be spinosad. Further disclosed are methods for preparing systems for use in controlling arthropod populations.

18 Claims, No Drawings

US 7,887,828 B2

DUAL ACTION ORGANIC FORMULATION TO CONTROL TWO STAGES OF INSECT PESTS

CROSS-REFERENCES TO RELATED APPLICATIONS

This application claims the benefit of U.S. Provisional Application No. 60/857,749, filed on Nov. 7, 2006, the teachings of which are expressly incorporated by reference.

STATEMENT REGARDING FEDERALLY SPONSORED RESEARCH/DEVELOPMENT

The U.S. Government has a paid-up license in this invention and the right in limited circumstances to require the patent owner to license others on reasonable terms as provided for by the terms of Grant No. 2006-33610-18426 awarded by the United States Department of Agriculture.

BACKGROUND

1. Field of the Invention

The present invention relates to systems and methods for controlling leaf-eating insect populations. More specifically, the present invention relates to methods and systems for controlling gypsy moth populations at the larval and adult stages utilizing a long lasting wax emulsion formulation for the controlled release of a larvicide and a mating disruption pheromone that can be mechanically applied using conventional spray equipment.

2. Background of the Invention

Chemicals secreted externally by an organism to send information to members of the same species, known as pheromones, are used extensively by arthropods to communicate with each other and can be used in strategies for pest management.

The direct management of insect pests using pheromones for mating disruption, or "attract and kill" approaches can provide excellent suppression of key lepidopteran pests in agriculture and forestry. Large-scale implementation projects have yielded significant reductions in pesticide use while maintaining acceptably low crop-damage levels. There are, however, some difficulties with high populations of pests.

The gypsy moth (GM), *Lymantria dispar*, is one of North America's most devastating forest pests. The species originally evolved in Europe and Asia and has existed there for thousands of years. In either 1868 or 1869, the gypsy moth was accidentally introduced near Boston, Mass. by E. Leopold Trouvelot. About 10 years after this introduction, the first outbreaks began in Trouvelot's neighborhood and in 1890 the state and federal governments began their attempts to eradicate the gypsy moth. These attempts ultimately failed and since that time, the range of the gypsy moth has continued to spread. Every year, isolated populations are discovered beyond the contiguous range of the gypsy moth, but these populations are eradicated or disappear without intervention. It is inevitable that the gypsy moth will continue to expand its range in the future.

The gypsy moth is known to feed on the foliage of hundreds of species of plants in North America but its most common hosts are oaks and aspen. Gypsy moth hosts are located through most of the coterminous United States but the highest concentrations of host trees are in the southern Appalachian Mountains, the Ozark Mountains, and in the northern Lake States. Gypsy moth populations are typically eruptive in North America; in any forest stand densities may fluctuate from near 1 egg mass per hectare to over 1,000 per hectare. When densities reach very high levels, trees may become completely defoliated. Several successive years of defoliation, along with contributions by other biotic and abiotic stress factors, may ultimately result in tree mortality. In most northeastern forests, less than 20% of the trees in a forest will die but occasionally tree mortality may be very heavy.

Because the females of the European gypsy moth form in the United States are unable to fly, natural spread is very limited. An estimated range expansion due to larval dispersal alone is only expected to be about 1.4 miles per year. The higher rate of spread of 13 miles per year that was observed from 1960 to 1990 is most likely the result of introductions that occur when humans accidentally move gypsy moth life stages into the transition or uninfested zones on outdoor household articles, nursery stock, vehicles, and other objects. These life stages establish colonies that reproduce and expand over successive years. Eventually these "spot" infestations coalesce with the continuously infested area, which produces a high rate of spread. A consortium led by the United States Department of Agriculture (USDA) Forest Service is controlling gypsy moth in the expansion front to reduce its rate of spread using management tools that are quite limited in flexibility and longevity.

Following a successful pilot project initiated in 1992, the USDA Forest Service, along with state and federal cooperators, implemented in 1999 the National Slow the Spread (STS) of the gypsy moth project across the 1,200 mile gypsy moth frontier from North Carolina through Minnesota. The goal of the STS project is to use novel integrated pest management (IPM) strategies in order to reduce the rate of gypsy moth spread into uninfested areas. Implementation of STS is expected to decrease the new territory invaded by the gypsy moth each year from 15,600 square miles to 6,000 square miles, protect forests, forest-based industries, urban parks, rural parks, and private property, and avoid at least $22 million per year in damage and management costs. This new IPM strategy is dependent upon intensive monitoring of low moth populations coupled with timely control of growing isolated populations. While traditional approaches to gypsy moth management address potentially defoliating populations occurring in generally infested areas, the STS project focuses on low-level populations in the transition zone between areas considered generally infested and generally uninfested.

The USDA, state and local governments jointly participate in programs to locate and eradicate new gypsy moth populations in currently uninfested areas. The project consists of a coordinated effort by the USDA (Forest Service and Animal and Plant Health Inspection Service (APHIS)) and nine state governments: North Carolina, Virginia, West Virginia, Kentucky, Ohio, Indiana, Illinois, Michigan, and Wisconsin. The annual cost to deploy the approximately 80,000 traps and treat approximately 275,000 acres is under $11 million. The benefits associated with the reduction in the rate of spread outweigh the cost of implementation by an estimated ratio of at least 3 to 1.

Grids of pheromone-baited traps spaced at two kilometer intervals are used for detecting isolated colonies in the transition zone, a band 100 kilometers wide spanning the entire length of the generally infested area in the United States. When moth captures in traps indicate a possible colony, a delimiting grid with 0.5 kilometer intertrap distance is set to delineate the boundary of the colony prior to treatment. This ensures aerial treatments are accurately targeted. Areas to be delimited or treated are initially determined by a computer algorithm designed to analyze moth capture patterns according to project standards and priorities. Then maps of the recommendations are posted on the Internet, which are used by federal and state representatives to begin planning actions that will be taken in the following year. Plans are discussed, prioritized, and finalized at the project level. The finalized plan of action is then compared to the initial computer recommendations to ensure compliance with project standards.

Widespread use of mating disruption, a noninsecticidal treatment, is one of the key elements in the STS project. Mating disruption is based on the application of controlled-release dispensers that emit an insect sex pheromone for several months. The pheromone emitted by the dispensers interferes with the normal mate-searching behavior of males. As a result, females are not mated and lay nonviable eggs.

There are currently two controlled-release products registered with the United States Environmental Protection Agency (EPA) that can be used to disrupt mating between gypsy moths. Disrupt® II is manufactured by Hercon Environmental (Emigsville, Pa., EPA Reg. No. 8730-55). The pheromone is injected between thin sheets of plastic, and then chopped into small pieces ($\frac{1}{32} \times \frac{3}{32}$ inches). Prior to application, the flakes are mixed with a sticker called Gelva (Surface Specialties UCB, Smyrna, Ga.) to ensure they will stick at all levels in the forest canopy where gypsy moths are found. The plastic flakes slowly release the pheromone into the environment over a 2-3 month period. The second is the 3M™ MEC (Microencapsulated) Sprayable Pheromone for gypsy moth manufactured by 3M™ Canada (London, Ontario, EPA Reg. No. 10350-62). The pheromone is encapsulated in small polymer capsules (5-100 μ in diameter) that are suspended in a thick liquid that preserves the formulation. The pheromone starts releasing through the capsule walls soon after the product is applied and continues to release for a period of up to 6 weeks.

Operationally, flakes are typically applied at a rate of 75 g a.i./ha based on the results of dose response studies conducted with ground-applied and aerially-applied disparlure.

As a result of gypsy moth mating disruption tests using hand applied pheromone dispensers positioned at 1.5 meters above the ground, it has been found that mating success in sentinel females was greater at a height of 15-20 meters than at 1.5 meters. Ground-applied pheromone dispensers fail to impact population growth, presumably because the pheromone does not sufficiently penetrate the canopy where mating takes place. Based on these results, it was concluded that pheromone dispensers must be distributed throughout the forest canopy for mating to be disrupted at all heights. This led to the development of equipment suitable for the aerial application of flakes with a sticking agent (sticker). Special pods mounted on each wing of the aircraft mix flakes and sticker just before dispersal through a spinner. It has been found that, using this system in an operational application of flakes with an effective sticker, approximately 25% of the applied flakes were deposited in the upper canopy, 28% in the middle canopy, 25% in the lower canopy, 12% on understory vegetation, and 10% on the ground.

Aerial pheromone application studies established that mating success declined as the application rate was increased from 7.5 to 75 g of disparlure/ha (or 30 g/a). Also, it has been demonstrated that 30 grams per acre suppresses mating in low-density populations. Recent experiments indicated that mating in low-density populations can be suppressed at even lower doses of 15, 6, and 3 grams per acre. Thus, in 2001-02 the recommended dose for the STS project, dealing with low-density populations, was reduced to 15 grams per acre, at a cost of approximately $17 per acre, which compares favorably with alternative treatments such as double applications of *B. thuringiensis* ($26-$28 per acre) or a single application of diflubenzuron ($12-$15 per acre). The current recommended doses for the STS project are 15 and 6 grams of active ingredient disparlure per acre. When using Hercon's Disrupt® II the recommended 15 grams is equivalent to 85 grams of flake formulation per acre mixed with two fluid ounces of sticker, providing 1 or 2 sticky flakes per square foot of canopy area. When using the 3M's MEC product, the 15 gram dose is equivalent to 2.6 fluid ounces of product mixed with water and applied at a rate of 1 quart per acre.

Mating disruption has shown to be as efficacious in control of isolated gypsy moth colonies as *B. thuringiensis* treatments, and the scope of its use in the STS project has increased dramatically. Target-specific tactics such as mating disruption will continue to be critical in STS to protect unique habitats and rare, threatened, or endangered species that occur within the project area.

The effectiveness of gypsy moth mating disruption with the current formulations, however, decreases with increasing gypsy moth population density, and there is evidence that the tactic is effective only when moth populations are sparse; which helps to explain the success of mating disruption in the STS program. Mating disruption as it is, however, doesn't seem to be a promising technology to take back the area in the east where the gypsy moth is already established.

Also, the current disparlure formulations are inefficient in their release of pheromone. For example the flake locks the disparlure, consequently more than half of the active ingredient remains unreleased at the end of the period of male moth flight. Only 27-40% of the applied pheromone is released during the period of male moth flight, or within 42 days after application. This indicates that if more efficient controlled-release formulations that dispense most of their pheromone were developed, the result would be a substantial reduction (as much as 60%) of the amount of disparlure applied per treated area without compromising the efficacy of disruption.

The use of new, more efficient formulations, or a reduction in the dose of the existing formulations, could reduce the amount of active ingredient required for control resulting in a reduction in the per acre cost of this control tactic.

Studies of the vertical profile of disparlure after an aerial application to forest canopies indicated that the vertical distribution of disparlure follows the vertical distribution of the dispensers. It follows that, when flakes are applied without sticker and mostly fall to the ground, there should be a lower concentration of disparlure in the canopy than when a sticker is used. The effect of the distribution of aerially applied dispensers on the effectiveness of mating disruption has been investigated. Strong evidence was produced that mating disruption is less effective when flakes are applied without a sticking agent. There is little effect of gypsy moth mating disruption in the canopy after an application of flakes to the forest floor, as would occur if flakes were applied without sticker. The proportion of wild egg masses collected in 1998 with more than 5% fertile eggs was significantly higher under the no-sticking agent treatment.

The problem is that the use of a sticking agent in aerial flake applications not only increases cost of materials, but it also requires the installation of rare, specialized delivery equipment to planes and helicopters. It also causes clogs in the system which results in spotty applications and frequent loss of proper calibration. Furthermore, there are situations in which it might be desirable to apply the pheromone formulation without sticker, such as over residential areas, to avoid damage of personal property (stickem creates a mess where it lands).

The application of Disrupt II requires specialized application equipment because of the glue and because of the large size and irregular shape of the flakes. These rare, special "pods" must be mounted on each wing of the aircraft, so that the flakes and sticker are mixed just before dispersal through a spinner to the forest floor. In addition to restricting application of pheromone to airplanes fitted with such specialized pods, pilots and field personnel complain that clogging of the system is a recurrent problem, resulting in higher than desired variation of MD applications.

Formulations of other materials such as microencapsulated materials, gels or wax emulsions, which can be applied with conventional spray equipment would open up competition among a larger group of aerial applicators and lead to a substantial reduction in application costs and facilitate operations which have to schedule every year the application of pheromone formulations in the more than half a million acres of forest in a short window of time.

Earlier tests involving a polymethacrylate bead or microencapsulated formulations (Decoy GM Beads, Biosys, Palo Alto, Calif.), which can be applied with conventional spray equipment, suggested that the pheromone release profile may be more favorable than that of the flake's, the microcapsules release a higher percentage of the pheromone. However, current tests with the 3M MEC indicated that microencapsulated formulations released pheromone too rapidly to maintain adequate emission rates from the application period throughout the period of male flight.

Treatments prescribed for suppression in areas under the STS program include the use of two biological insecticides, the bacteria *Bacillus thuringiensis* variety *kurstaki* (*B.t.k*) and the gypsy moth nucleopolyhedrosis virus (Gypchek®), and one synthetic chemical insecticide, diflubenzuron (Dimilin®). Here we further suggest the use of Spinosad, an organic insecticide proven to be a highly effective larvicide on *Lymantria dispar* with extraordinary knockdown activity, as discussed below.

Gypchek®, containing the gypsy moth nucleopolyhedrosis virus is the only available insecticide that is target-specific to the gypsy moth. When gypsy moth larvae ingest the product containing the virus, it invades the gut wall and attacks the tissues, causing death. Gypchek® has been used extensively in the STS program and has not been found to affect any other species but the gypsy moth larvae, both in laboratory and field tests. Gypchek® is not known to have any adverse human health risks. If adequate supplies were available, this would be the best insecticide to use to avoid non-target species impact.

In most STS cases, two applications of Gypchek® are sufficient to achieve defoliation prevention. The typical application rate of Gypchek® is 1011 occlusion bodies/acre. Low-flying aircraft (fixed wing or helicopters) apply this pesticide to tree canopies in separate flights during the 2nd and 3rd larval instars.

B.t.k. is less specific and will affect other lepidopteran (butterfly and moth) larvae that are feeding during the treatment period. It is not known to have significant direct effects on any other orders of animals or plants. These bacteria contain a crystalline structure that when eaten acts as a stomach poison to the larvae of many species of butterfly or moth that feed on treated leaf tissue and get a lethal dose. Only lepidopterans that are feeding during this active period may suffer mortality. The impact is also lessened somewhat when applied in a patchwork fashion to highly infested areas. This allows non-target lepidopterans in adjacent non-treated forests to migrate into treated areas throughout the remainder of the season. In most STS cases, a single application of B.t.k is sufficient to achieve defoliation prevention. Typical application rates of B.t.k. are 36 BIUs/acre. Low-flying aircraft (fixed wing or helicopters) apply this pesticide to tree canopies during the 2nd and 3rd larval instars.

Diflubenzuron is the least specific and potentially most detrimental pesticide of the three recommended by the Forest Service.

Spinosad is a novel, natural insecticide derived from *Saccharopolyspora spinosa* Mertz & Yao, a new *Actinomycetes* species isolated from soil sampled at a sugar mill rum still. Spinosad is a mixture of two complex organic molecules, spinosyn A ($C_{41}H_{65}NO_{16}$) and spinosyn D ($C_{42}H_{67}NO_{16}$), and it is produced by Dow Agrosciences (DAS). DAS indicates that spinosad is primarily a stomach poison with some contact activity; it has broad-spectrum activity across insect orders, and it is particularly effective against Lepidoptera and Diptera; little or no toxicity to mammalian and avian species; and favorable environmental characteristics. Spinosad has a novel, neurotoxic mode of action which causes rapid paralysis and cessation of feeding. Laboratory and field evaluations indicate that gypsy moth larvae are highly susceptible to spinosad. Bioassays using red oak leaf disks treated with spinosad in a Potter spray tower yielded an LC50 value of 0.0015 mg AI/cm2 (3-day exposure; 13-day evaluation; 2nd instar larvae). Applied to foliage to run-off in the laboratory (potted red oak seedlings) and the field (4 m-tall birch trees), spinosad effectively controlled 2nd instar larvae at concentrations ranging from 3 to 50 mg/liter.

Laboratory studies supported field observations that control was achieved in part by knockdown due to paralysis. In addition, laboratory results demonstrated that crawling contact activity may play an important role in field efficacy as 50% of treated larvae were paralyzed 16 hours after a 2 minute crawling exposure to glass coated with a 4 mg/litre spinosad solution. It has been found that toxicity in the laboratory, and efficacy and persistence in the field, were comparable to those achieved with permethrin. Spinosad at concentrations in the range 3±50 mg/litre applied to run-off will effectively control gypsy moth larvae in ornamental style applications. At these concentrations control was achieved quickly, larval populations were reduced by 95±100%, and residual activity was high. Even an application rate of 0.75 mg/litre eventually resulted in large population reductions. They found that contact with low Spinosad concentrations caused paralysis (by letting larvae crawl on contaminated surfaces for two minutes), rather than rapid mortality, of gypsy moth larvae. Although recovery after exposure by crawling contact activity to low doses may be possible, it is very unlikely that weak larvae falling from trees in the field will survive to mate and reproduce.

The principal reported activity of spinosad in Lepidoptera is caused by ingestion, not contact. Thus the high knockdown effect on gypsy moth larvae following transient contact with spinosad is remarkable.

Gypchek® is preferred over B.t.k. as a treatment option primarily due to its host specificity. However, Gypchek® is available only in limited amounts because of a specialized production process that requires the use of live gypsy moth larvae. Gypchek® supplies are manufactured and distributed by the Forest Service, and no commercial source is yet available. The Forest Service has set a clear priority for the use of Gypchek® in the protection of federally endangered and threatened species and other sensitive areas. Gypchek® has been made available to the STS program, but its future availability remains uncertain.

Pesticides must be applied just after the emergence of the gypsy moth caterpillar in early May. In some areas where the gypsy moth population is high, as indicated by egg mass sizes and numbers, the Forest Service recommends an additional B.t.k. application 5-7 days after the initial treatment to ensure successful population suppression. The short life of Gypchek® also calls for two applications in separate flights during the 2nd and 3rd larval instars.

The larvicidal effect of all formulations mentioned above, Gypcheck, B.t.k., Diflubenzuron, and Spinosad, are severely shortcut if application is followed by rain. The washing of the chemical from the leaves and trunk of the trees by rain drastically decreases the probability of gypsy moth larvae encountering a high enough dose of larvicide for the effect of the contact or stomach poison to take place.

Because of the short life of the current larvicide formulations, timing of the application is everything: low-flying aircraft (fixed wing or helicopters) must apply these pesticides to tree canopies during separate flights during the 2nd and 3rd larval instars.

Enhancement of longevity and rainfastness of these formulations, even if only for two to four months, would make it easier to guarantee that the larvicide would be present in every high-risk-area detected, in anticipation of the larvae hatching from overwintering egg masses. One of the major advantages would be the extension of the window of opportunity for the timing of the sprays, thus easing the scheduling and execution of the larvicidal sprays: planes would be able to, based on each area's egg mass sizes and numbers, start spraying targeted areas weeks, perhaps a month or more in advance, before the larvae emerge.

Based on the considerations above, we believe that Spinosad might be the best candidate larvicide to be formulated with the Specialized Pheromone and Lure Application Technology for Gypsy Moth (SPLAT GM) of the present invention because of the strong knockdown effect on gypsy moth larvae, at low, economically viable doses; it is produced commercially and in large quantities, is labeled organic and registered for "all crops"; and it is a stable molecule (once UV-protected and anchored by SPLAT).

For the suppression of gypsy moth in areas under protection of federally endangered and threatened species act and other sensitive areas the candidate larvicide to be formulated with SPLAT GM could be Gypchek®.

BRIEF SUMMARY

The present invention is directed toward systems and methods for controlling arthropod populations at both immature and adult stages. The systems and methods of the present invention utilize insecticides that are toxic to an immature stage arthropod along with a semiochemical that is reactive upon an adult stage arthropod.

One embodiment of the present invention is directed toward a dual-action system for controlling arthropod populations. The arthropods are characterized by both a plant-feeding immature stage and a semiochemical-affected adult stage. The system of this embodiment includes a polymeric substrate, a semiochemical, and an insecticide. The semiochemical is reactive upon the adult stage arthropod and is intermixed within the polymeric susbtrate. The insecticide is of the per os (taken by mouth) variety, is toxic to the immature stage of the arthropod, and is also intermixed within the polymeric substrate. The semiochemical may be a pheromone, and may specifically be a sex pheromone that disrupts the mating behavior of the adult arthropod. As such, the system is capable of acting on two different life stages of the arthropod in two different manners, i.e., by the semiochemical that interferes with processes of the adult stage as well as an insecticide that is toxic to the immature stage. The immature stage may be a larval stage of, for example, lepidopteran insects and coleopteran insects.

The polymeric substrate may be present in numerous different configurations, including, but not limited to, microspheres, latex solutions, hot melt glues, resins, plastic flakes, and wax emulsions. The waxes that may be used in the wax emulsion include, but are not limited to, paraffin wax, carnauba wax, beeswax, candelilla wax, fruit wax, lanolin, shellac wax, bayberry wax, sugar cane wax, microcrystalline wax, ozocerite, ceresin, montan wax, and combinations thereof. The hot melt glues include, but are not limited to, glues including ethylene-vinyl acetate, polyethylene, polypropylene, a polyamide, or a polyester. One wax emulsion may be made up of 30% paraffin wax, 4% soy oil, 2% Span 60, 1% vitamin E, and distilled water. Another wax emulsion envisioned by the present invention includes 45% microcrystalline wax, 6% soy oil, 3% Span 60, 1% vitamin E, and distilled water.

The semiochemical may be dissolved within the polymeric substrate, including within wax emulsions. As discussed above, the semiochemical may be a pheromone, or more specifically, may be a sex pheromone. One particular sex pheromone that may be utilized is disparlure. When disparlure is used, it may be present in the system in a range between about 0.03% by weight to about 3.0% by weight. More particularly, the disparlure may be present in the system in an amount of about 1.5% by weight. The system may further include a second semiochemical. This second semiochemical may be intermixed within the polymeric substrate and may be reactive upon the immature stage of the arthropod. More particularly, the second semiochemical may be an attractant or phagostimulant to the immature stage arthropod.

The insecticide may be dissolved within the polymeric substrate, including within wax emulsions. The insecticide may be a per os insecticide wherein the insecticide is capable of being ingested by the immature stage of the arthropod. One per os insecticide that may be used in spinosad. The spinosad may be present in the system in an amount of about 0.4% by weight. Exemplary insecticide types that may be used in the present invention include, but are not limited to bacterial, organophosphates, carbamates, pyrethroids, chloronicotinyls, and other types. Some bacterial insecticides that may be used with the present invention include, but are not limited to, spinosad, abamectin indoxacarb, emamectin benzoate *Bacillus thuringiensis* var. *israelensis, Bacillus thuringiensis Aizawai*, and *Bacillus thuringiensis* var. *kurstaki*. Some organophosphate insecticides that may be used with the present invention include, but are not limited to, terbufos, dimethoate, disulfoton, oxydemetonmethyl, phorate, acephate, parathion, and monocrotophos. Some carbamate insecticides that may be used with the present invention include, but are not limited to, carbofuran, aldicarb, and carbaryl. Some pyrethroid insecticides that may be used with the present invention include, but are not limited to, cypemethrin, permethrin, deltamethrin, and cyfluthrin. Some chloronicotinyl insecticides that may be used with the present invention include, but are not limited to, thiamethoxam, imidacloprid, and acetamiprid. Diatomaceous earth may also be used as an insecticide in the present invention. Although it is contemplated that the present invention utilizes per os insecticides that are ingested by the immature arthropod, the present invention does not exclude the use of insecticides that may also have contact toxicity, especially insecticides that exhibit only minor contact toxicity as opposed to a primarily per os toxic effect.

Although the system may be utilized to control the population of a wide range of arthropods, this embodiment is also well suited for controlling insect populations, and more particularly, lepidopteran and coleopteran populations. The system may be in a fluid form conducive to use within conventional aerial spray equipment. The system may be prepared so as to release the pheromone and insecticide over a long period of time, for example, over a 2-4 month period.

Another embodiment of the present invention is directed toward a method for controlling the population of an arthropod in a region. The arthropod is characterized by having both a plant-feeding immature stage and a semiochemical-affected adult stage. In this method, a system is administered to a forest canopy of a region to be treated. As used herein, the forest canopy includes not only the uppermost level of a forest, but also the outer layers of individual trees, orchards, gardens, and individual plants. The system administered to the forest canopy is of the type described above, that is, the system is made up of a polymeric substrate, a semiochemical, and a per os insecticide. The semiochemical is reactive upon the adult stage of the arthropod and is intermixed within the polymeric substrate, while the per os insecticide is toxic to the immature stage of the arthropod and is also intermixed within the polymeric substrate.

The system may be administered by aerial spray equipment. Furthermore, the system may be administered by conventional aerial spray equipment mounted on fixed-wing aircraft or rotorcraft. The system may also be administered by terrestrial-based methods. For example, the system may be administered by terrestrial-based spraying systems or by dispersing the system by way of "paintballs."

The method enables the novel effect of both interfering with the behavior of the adult stage arthropod as well as being harmful to the immature stage of the arthropod. As such, the method controls the population of the arthropod by interacting with two life stages of the arthropod. Accordingly, the system may be administered during the immature stage of the arthropod and by being in the form of a controlled-release, rainfast, substance, the system remains present until the adult stage of the arthropod is reached. For example, in the case of controlling gypsy moth populations, the system may be administered in the spring (e.g., late April or early May) and the system may remain within the forest canopy of the region for at least four months thereby being present during the entire life cycle of the gypsy moth and being present to interfere with both the immature larval-stage and the adult-stage of the gypsy moth. Accordingly, the per os insecticide may kill or harm the larval-stage gypsy moth so that reproduction does not occur thereby reducing the number of gypsy moths that reach the adult stage. Further, the same system remains present in the region and the semiochemical may disrupt the mating behavior of any adult-stage gypsy moths present thereby reducing the number of fertilized gypsy moth eggs in the region.

As discussed above, the semiochemical may be a pheromone, or more particularly may be a sex pheromone. One sex pheromone envisioned for use in the method is disparlure. One per os insecticide envisioned for use in the method is spinosad. One particular embodiment of the method includes administering the system to the region such that each hectare, or subparcel, of the region is administered 15 grams of disparlure and 4 grams of spinosad.

Another embodiment of the present invention is directed toward a method of preparing a dispersible system for use in controlling the population of arthropods. The steps of this method include providing a polymeric substrate, adding a semiochemical to the polymeric substrate, and adding an insecticide to the polymeric substrate. The semiochemical is reactive upon an adult stage arthropod. Also, the insecticide is toxic to an immature stage arthropod.

Furthermore, the semiochemical may be a pheromone. In particular, the pheromone may be a sex pheromone. One particular sex pheromone that may be utilized is disparlure. The insecticide may be a per os insecticide, and more particularly may be spinosad.

The polymeric substrate may be a wax emulsion. In this embodiment, the wax emulsion may be formed by melting a wax, adding an oil, emulsifier, preservative, and water heated above the melting temperature of the wax to the melted wax to form a wax emulsion, and cooling the wax emulsion. Although many waxes are contemplated, the waxes may include, but are not limited to, paraffin wax and microcrystalline wax. Additionally, the oil may be soy oil, the emulsifier may be Span 60, and the preservative may be vitamin E.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Semiochemical formulations should exhibit a zero-order-release rate and sustain release levels above a certain threshold for a long period of time, wherein release levels below threshold would only have a negligible disruptive effect on the behavior of the target insect. With a couple of exceptions, when formulated with less than 10% active ingredient (AI) Specialized Pheromone and Lure Application Technology (SPLAT) consistently provides a near zero-order-release rate of the semiochemical, with negligible flash-off around the time of application.

The initial research and development that culminated into the existing SPLAT technology was done using *Grapholita molesta*, the Oriental fruit moth (OFM), a serious pest of apples worldwide, as the model insect. When formulated with less than 10% OFM pheromone, SPLAT consistently provided a near zero-order-release rate with negligible flash-off. Field trials in large commercial apple operations in South America indicated that SPLAT formulations containing 15 g pheromone per acre sustained nearly complete trap shutdown for over 180 days, which actually translated in a significant reduction of OFM fruit damage, as compared to that found in the grower's traditional chemical control. Analysis of the field "aged" SPLAT indicated that there were different levels of pheromone remaining in the point source of SPLAT by the end of the 180 day trial period, and it was related to the position of the dollop in the canopy (receiving more or less solar incidence) as well as the actual size of the dollop analyzed: pheromone in microdollops was undetectable, whereas 1 g dollops still contained 5-10% and 5 to 10 g dollops retained between 10 and 25% AI.

Furthermore, we found out that the addition of contact insecticides (e.g., pyrethroids, OPs) to the SPLAT OFM formulations increased both their efficiency and longevity (as population suppressants). We also found that SPLAT formulated with attractants, phagostimulants and a stomach poison, such as Spinosad, proved to efficiency and longevity as an attract and kill agent targeting one or several species of fruit flies.

In the case of gypsy moth we believe that an attract and kill formulation with a generic contact insecticide might pose a risk to the STS program (e.g., lawsuits) that is higher than acceptable, because of the large areas being treated, because of the effects on non-target species, and because some of the treated areas are urban or semi urban. It would be acceptable; however, if in addition to the mating disruption effect the SPLAT GM would also have a larvicidal effect. This larvicidal effect could be achieved by the addition to SPLAT of a safe, organically certified, insecticide such as Spinosad or GypCheck, a baculovirus formulation recommended and used by the STS program. The application of SPLAT GM could occur in early spring, on young leaves in late April or early May, thus reducing the number of larvae, and by remaining in place emitting pheromone also disrupt mating of emerging adults from July to August.

This novel formulation, a SPLAT Disparlure formulation that is larvicidal and mating disruptant, can be applied using conventional defensive application apparatus, will last for 4 months or longer in the field, releases nearly all the pheromone it contains, and is biodegradable and safe.

This formulation will be revolutionary providing the US forest service with the ease of use and substantial savings. The cost of SPLAT with the equivalent to Disrupt II 15 g disparlure/hectare and with Spinosad at 4 mg/hectare will be about $30 dollars per hectare, which represents a savings of $12 per hectare just considering the cost of Disrupt. Now, if this formulation also substitutes the customary two treatments of B.t.k. at a cost of $64-69/ha, then the savings will be $39/ha. The treated areas are vast, and based on the historical use of MD and B.t.k., the savings from the use of SPLAT GM in a four year period would translate into $27,429,528 in pheromone applications and $20,943,507 in b.t.k. applications for a total savings of $48,373,035 that the STS program could have exercised if SPLAT GM had been used.

Our calculation of the savings is very conservative. It does not take in account the additional savings to the STS program that will be achieved by having more competitors bidding to provide services and aerial applications; or the savings realized because of the simplification of the STS control operation, with a single dual action solution for larvae and adults, a formulation with such a long life that it allows for a single application for the entire gypsy moth cycle. More savings will be achieved by elimination of crisis situations and their associated cost. Furthermore, we believe we overestimate the cost of manufacturing SPLAT. It is probably high because it is based on the price we currently pay our suppliers, which do not reflect the discounts available from commercial suppliers when we purchase the raw materials in large bulk quantities. Furthermore the efficiency of the production line increases with the larger volumes, needing less worker hours per volume of SPLAT produced. These additional savings have not been accounted for.

It is possible that, because of its dual action, SPLAT GM could provide population control not only in areas of low and medium population densities, such as in the expansion front, but also allow us to reclaim those areas with historically high gypsy moth population levels east of the expansion front, providing a huge benefit to the forestry industry and population in general. So, if we consider the other consumer markets for the infested areas, then the savings and benefits to the United States taxpayers and forestry industry would be substantially larger than stated.

It is believed that the ideal disparlure formulation should be applied using conventional spray equipment, have a duration of at least two to three months, stick to the foliage where it lands, quickly acquire rain-fast qualities, protect the pheromone from degradation, work synergistically with adulticides so that it can possibly control gypsy moth populations at low as well as at high densities, be biodegradable, if possible organic, not damage private property, and last but not least the formulation should be inexpensive for its adoption to be not only technically, but also economically feasible.

The present invention is expected to meet all of the desired factors by providing an optimal semiochemical solution for the effective management of gypsy moth independent of population density. Here we brought up the innovation of using a larvicidal agent together with the mating disruption formulation. The overall objective of this invention is to provide effective season-long field control of gypsy moth populations using a flowable wax emulsion system (SPLAT) that delivers both the sex pheromone disparlure and a larvicidal agent. We formulated SPLAT GM using flowable wax emulsions of different characteristics in order to determine in the lab the emission rate and stability of the pheromone and the stability of the larvicide. Two of the optimized formulations were submitted to field trials to which we added high gypsy moth pressure. Field aged samples of the SPLAT formulations were analytically quantified and bio-assayed to determine residual stability and effectiveness of pheromone and the larvicide components.

Some of the goals of the invention include: 1) a formulation having a duration of four months while being protected from degradation while dispensing disparlure; 2) a formulation that works synergistically with killing agents; 3) a formulation of SPLAT that works with conventional aerial spray equipment, sticks to foliage and quickly becomes rain-fast; and 4) a formulation that controls gypsy moth populations at low as well as high densities. However, it is contemplated that in some embodiments of the invention only some, or even none, of the goals may be achieved.

The SPLAT GM pheromone release formulation, a novel, amorphous, flowable emulsion can be applied as microliter point sources all the way to dollops of tens of grams. The SPLAT wax dispenser formulations of this invention belong to a "matrix-type" or "monolithic" category of controlled-release devices. These "matrix-type" or "monolithic" dispensers are defined as devices where the active ingredient is dispersed or dissolved in a polymer matrix. Release of the active ingredient from a monolithic device occurs by diffusion and can be described macroscopically by Fick's Law. Fick's law states that the movement of a molecule by diffusion is directly proportional to the concentration of that molecule in a system. Microscopically, if we follow the movement of a molecule of an active agent through a matrix, this molecule can begin its journey in one of two ways. If it is dispersed in the matrix, it begins its journey by dissociating from other molecules in its crystal cell and solubilizing into the polymer phase. If it is dissolved in the matrix, then this step is bypassed. The molecule then diffuses through amorphous regions in the matrix that comprise the free volume of the system. The molecule can move through the matrix in one of two ways as well. If it is very small compared to the size of the amorphous spaces in the matrix, then it will diffuse through the matrix by moving from one such space to another. If it is very large compared to the size of those spaces, then segments of the polymer comprising the matrix will have to be rearranged for diffusion of the active agent molecule to occur. Crystalline regions in the matrix are virtually impermeable to molecules of the active agent. Upon reaching the surface of the matrix, it will be released into the environment.

A series of factors influences the rate of release of an active agent from a monolithic device and includes properties of the matrix material as well as properties of the active agent. The temperature of the matrix influences release of the active agent; at higher temperatures the free volume is increased, and diffusion occurs faster. At lower temperatures, the free volume is decreased, and diffusion is slower. The thermal history of a polymer can also increase or decrease the free volume of the system and lead to changes in the diffusional rate of an active agent.

The property of the active agent having the greatest influence on its release rate is its molecular weight. Generally, larger molecules take more time to make their way through the free space of a matrix. Branching in a molecule can also decrease its rate of diffusion through a matrix. The partition coefficient of the active agent between the matrix and the environment can also influence the release rate of that agent. If the agent readily partitions to the environment, then its rate of release will be diffusion-controlled and first order. If, however, partitioning of the active agent to the environment is relatively slow, then its partition coefficient will determine its release rate from the matrix and the device will exhibit zero order release kinetics. The partitioning of the active agent to the environment is a function of the solubility of the active agent in the matrix; compounds more soluble in the matrix partition to the environment more slowly. SPLAT paraffin emulsions in a field environment exhibit diffusion-controlled release. The surface area of the device also influences its release rate. Paraffin dispensers with larger surface areas release active agent at faster rates.

The release rate of a SPLAT formulation containing a fixed amount of semiochemical can be modulated simply by changing a few of parameters of the formulation, which includes the type of components used (e.g. the wax composition, the emulsifiers used), their proportion in the formulation (e.g., percentage of water, oil or wax content), the stage in the manufacturing the different components are added, the rheology, and finally the characteristics of application of the SPLAT in the field (e.g., applied as microdollops of 1-10 ug each or large dollops of 10 g each).

The result is a semiochemical formulation that is extremely malleable and that fits many needs and uses that cannot be supported by any other commercial formulation present in the market.

A 30% paraffin wax emulsion was made consisting of 30% paraffin wax (Gulf Wax, Royal Oak Sales, Inc., Roswell, Ga.), 4% soy oil (Spectrum Naturals, Inc., Petaluma, Calif.), 2% Span 60 (Sorbitan monostearate, Sigma-Aldrich Co., St. Louis, Mo.), 1% vitamin E α-tocopherol, Sigma Chemical Co., St. Louis, Mo.), and 58% distilled water. A 45% microcrystalline wax emulsion consisting of 45% microcrystalline wax (Blended Waxes, Inc., Oshkosh, Wis.), 6% soy oil, 3% Span 60, 1% vitamin E, and 40% distilled water was also made.

The wax is melted (paraffin: 60-65° C.; microcrystalline: 78-80° C.) and water heated above the melting temperature of the wax (paraffin emulsion: 65-70° C.; microcrystalline emulsion: 78-88° C.). The soy oil, Span 60, and vitamin E are added to the melted wax and thoroughly mixed, followed by the addition of the hot water. This mixture is then poured into a industrial laboratory blender. The emulsion is immediately blended, then placed in a cold water bath, and mixed every 15 minutes until the solution had cooled to 25-30° C. when it is placed in a plastic bucket and stored until use.

Just prior to use, 0.03% (3 g), 1.0% (10 g) and 3.0% (30 g) by weight of emulsion of racemic disparlure (ISP) is thoroughly mixed into the emulsion using a high sheer lab mixer.

Preliminary work with generic SPLAT formulations containing 3% racemic disparlure using flow cells indicates that it releases pheromone at a very constant level for long periods. We collected the effluvia from 5 g SPLAT GM 3%, containing 150 mg disparlure and found that it released disparlure at a rate of 44.06±13.08 ug/day for over ca. 170 days. As a comparison, 5 g of Disrupt II, containing 894 mg disparlure emit 51.45±2.33 ug/day. It is important to realize that although both flow chambers had 5 grams of formulation, Disrupt II actually had six times more pheromone than SPLAT while it released only 15% more pheromone than SPLAT, a difference that probably has no biological effect to speak of. These results suggest that SPLAT is a much more efficient formulation than Disrupt II in the controlled-release of disparlure; actually six times more efficient. As such, one would need to apply six times less disparlure using SPLAT than if using Disrupt II. Usually the most expensive component of a mating disruption formulation is the active ingredient, in this case the disparlure. Accordingly, SPLAT is believed to be substantially less expensive than the formulations of the prior art.

A larvicide 0.4% (4 g/kg) by weight of emulsion of Technical Spinosad (DAS) was added to generic SPLAT and to SPLAT Disparlure by being thoroughly mixed into the emulsion using a high sheer mixer. SPLAT applied together with disparlure and a larvicide effectively kill $3^{rd}$ and $4^{th}$ larval instar of gypsy moth, which is a very difficult stage to kill. Furthermore, the pheromone needed for mating disruption does not result in a reduction of the killing effect of the gypsy moth larvae.

With SPLAT, one can change the consistency of the emulsion by changing the proportion of components, or by changing the rheology of the mixing of the components. The word "rheology" normally refers to the flow and deformation of "non-classical" materials such as rubber, molten plastics, polymer solutions, slurries and pastes, electrorheological fluids, blood, muscle, composites, soils, and paints. These materials can exhibit varied and striking external and internal structures due to their rheological properties that classical fluid mechanics and elasticity cannot describe. Our experience is that the SPLAT formula with 45% microcrystalline wax emulsion (45% microcrystalline wax, 6% soy oil, 3% Span 60, 1% vitamin E, and 40% distilled water) can be mechanically applied and that it adheres quickly to the vegetation, and as long as it has a couple hours to settle, it becomes rain fast.

High-sheer, high-speed mixing regimens can be used in order to create highly flowable formulations that can be easily handled by the pumping system of spray planes. By modulating the time and/or speed and/or sheer (dictated by the type and number of blades used) of the mixing one can reliably create formulations of different densities and flow characteristics.

Using approximately 20 gallons of each type of formulation for test flight situations, a Cessna Ag-Truck equipped with a standard commercial spraying system was operated by an APHIS pilot who was highly experienced with precision work for research. The aircraft was also equipped with differentially corrected guidance and recording systems. However, primary guidance was provided by ground personnel that measured each swath and gathered meteorological data during application. The aircraft was additionally equipped with winglets (DBA-Ag Tips; Clark Oberholtzer, Alberta Canada). Prior to application, the aircraft spray system was calibrated to operate under parameters which resulted in delivery of spray within one percent of the desired rate per acre for each of the treatments applied. During calibration with generic SPLAT, temperatures of the formulated material ranged from 80° F. to 96.2° F. in the hopper of the aircraft. The air-applied SPLAT settled quickly to the plants to which it was applied.

Specialized Pheromone & Lure Application Technology (SPLAT) is a base matrix formulation of biologically inert materials used to control the release of semiochemicals and/or odors with or without pesticides. Extensive research on SPLAT using a variety of lures demonstrates that this matrix emits semiochemicals at effective pest suppression levels for a time interval ranging from 2-16 weeks. Having a wide range of viscosities and application methods (e.g. applicator sprays, aerial applicator sprays, caulking gun type tubes, etc.), SPLAT increases productivity by mechanizing the application of pheromone dispensing points. The amorphous and flowable quality of this highly adaptable product allows for an easy transition from small-scale manual applications to large-scale mechanical applications.

As discussed in detail before, there are no Disparlure formulations in the market today that have high longevity and that can be applied using conventional spray equipment. The present invention is an optimal semiochemical solution for the effective management of gypsy moth independent of population density. The present invention is effective in season-long field control of gypsy moth populations using a flowable wax emulsion system (SPLAT) that delivers both the sex pheromone disparlure and a larvicidal agent. The release rate of disparlure from two formulations of SPLAT, one with 10% of pheromone in the splat composition and the other with 13% of pheromone in the splat composition, applied in the field as point sources at three sizes, 1-5 mg, 15 mg and 100 mg each was measured. The SPLAT formulations retained and continued emitting pheromone for 60 days, with the formulations still retaining 30%-80% of its pheromone (depending on dose and point source size). This suggests that these formulations would probably last another 30 to 1209 days in the field (depending on dose and point source size). This indicates that if the formulation is sprayed in the field at the time of larval infestation, it will last until the end of the adult flight. This allows for the first time a formulation that can be sprayed to control the larvae of gypsy moth while also subsisting in the field to promote mating disruption through the emission of effective rates of pheromone during adult flight. This is a novel (it joins a larvicidal together with a pheromone that promotes mating disruption or attract and kill), revolutionary formulation that achieves results never seen before.

The invention may be utilized in the border of expansion (i.e., the STS project area) as well as in the areas where gypsy moths have been already established. In addition to the mechanically sprayed formulation, in order to increase the easiness in deployment in urban areas, the wax matrix may be used in a "paintball" formulation.

This embodiment is a novel pest management procedure for Gypsy moth control (mating disruption and larvicide), but may also be used in the management of other pests. The present invention provides an economical and effective method to control gypsy moth under the STS. Reduced insecticide use while retaining efficacy in control, is a major aim of the USDA and other federal and state agencies. The use of the gypsy moth-specific pheromone plus spinosad formulations of the present invention will protect natural resources by increasing specificity control actions, and by reducing the amount of toxic pesticides applied to achieve control. These two benefits will result in minimal impact on non-target organisms and will allow reduction of the application rates of active ingredients, so minimizing runoff and non-target toxicity problems. The problem of bio-magnification through the food chain as observed with other insecticides will be reduced due to the lower doses of insecticide used.

By targeting gypsy moths with an organic, safe, and effective formulation, non-target organisms will be minimally affected by any extra insecticide use, so insect species diversity will be retained where the semiochemical formulation is used. This in turn will conserve vertebrate animals that depend upon insects for their diet. The flora and fauna will be left to return to its original condition and to flourish for the pleasure of the public and the importance of retaining ecological diversity.

In one embodiment of SPLAT GM the Spinosad and the pheromone last for the whole season, but just for the gypsy moth season, not longer, to avoid unwanted residual problems and exposure to non-target species. The systems and methods of the present invention may be utilized for a plethora of other pests and invasive species (e.g., Fruit Flies, Sirex Wasps, PBW and others).

The present invention may allow for easier, more economical, ways to apply pheromone in the field. The present invention may be dispersed via aerial applications (using conventional equipment). Furthermore, the use of paint balls guns to deploy the formulation may be used in urban areas (as well as other areas) for the deployment of mating disruption or attract-and-kill formulations to tall or hard-to-reach structures such as many Palm and Nut trees. With the use of paintball guns, a single worker can precisely deploy more than 20 evaporators per minute onto the trunk or canopy of tall trees. Although described herein in relation to gypsy moths, the systems and methods disclosed herein may be utilized to control the populations of diverse pest species, such as codling moth in walnuts, the Med Fly in tropical countries, etc. It may also be used in the management of vertebrates, such as pigeons and rats, with repellent pellets precisely placed on hard-to-reach places.

The above description is given by way of example, and not limitation. Given the above disclosure, one skilled in the art could devise variations that are within the scope and spirit of the invention disclosed herein, including various polymeric substrates for carrying the semiochemical and insecticide. Also, the present invention can be used to control the populations of a wide variety of animals, including a broad spectrum of arthropods. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A dual-action system for controlling arthropod populations, the arthropod being characterized by a plant-feeding immature stage and a semiochemical-affected adult stage, the system comprising:
   a polymeric or wax substrate selected from the group consisting of a wax emulsion, microspheres, a latex solution, hot melt glue, a resin, and plastic flakes;
   disparlure intermixed within the substrate, wherein the disparlure is present in the system in a range between about 0.03% by weight to about 3.0% by weight and
   spinosad intermixed within the substrate, wherein spinosad is present in the system in an amount of about 0.4% by weight.

2. The system of claim 1, wherein the polymeric substrate is a wax emulsion.

3. The system of claim 2, wherein the wax emulsion is comprised of a wax carrier selected from the group consisting of paraffin wax, carnauba wax, beeswax, candelilla wax, fruit wax, lanolin, shellac wax, bayberry wax, sugar cane wax, microcrystalline wax, ozocerite, ceresin, montan wax, and combinations thereof.

4. The system of claim 3, wherein the wax emulsion comprises:
30% by weight paraffin wax;
4% by weight soy oil;
2% by weight sorbitan monostearate
1% by weight vitamin E; and
58% by weight distilled water.

5. The system of claim 3, wherein the wax emulsion comprises:
45% by weight microcrystalline wax;
6% by weight soy oil;
3% by weight sorbitan monostearate;
1% by weight vitamin E; and
40% by weight distilled water.

6. The system of claim 2, wherein the disparlure and the spinosad are dissolved within the wax emulsion.

7. The system of claim 1, wherein the substrate is hot melt glue.

8. The system of claim 7, wherein the hot melt glue is comprised of a polymer selected from the group consisting of ethylene-vinyl acetate, polyethylene, polypropylene, a polyamide, or a polyester.

9. The system of claim 1 wherein disparlure is present in an amount of about 1.5% by weight.

10. The system of claim 1 further comprising a second semiochemical intermixed within the substrate, the second semiochemical being an attractant or phagostimulant to an immature stage arthropod.

11. The system of claim 1, wherein the arthropod is an insect.

12. The system of claim 11, wherein the insect is a lepidopteran.

13. A method for controlling the population of an arthropod in a region, the arthropod being characterized by a plant-feeding immature stage and a semiochemical-affected adult stage, the method comprising:
administering a system to a forest canopy of the region, the system being comprised of: a polymeric or wax substrate selected from the group consisting of a wax emulsion, microspheres, a latex solution, hot melt glue, a resin, and plastic flakes;
disparlure intermixed within the substrate, wherein the disparlure is present in the system in a range between about 0.03% by weight to about 3.0% by weight; and
spinosad intermixed within the substrate, wherein spinosad is present in the system in an amount of about 0.4% by weight.

14. The method of claim 13, wherein the system is administered by either aerial spray equipment mounted on fixed-wing aircraft or rotorcraft or by a terrestrial-based spraying system.

15. The method of claim 13 wherein the system is administered such that each hectare of the region is administered 15 g disparlure and 4 g spinosad.

16. A method of preparing a dispersible system for use in controlling the population of arthropods, the method comprising: providing a polymeric or wax substrate selected from the group consisting of a wax emulsion, microspheres, a latex solution, hot melt glue, a resin, and plastic flakes;
adding disparlure to the substrate, wherein the disparlure is present in the system in a range between about 0.03% by weight to about 3.0% by weight;
and adding spinosad to the substrate, wherein spinosad is present in the system in an amount of about 0.4% by weight .

17. The method of claim 16, wherein the polymeric substrate comprises a wax emulsion, the wax emulsion being formed by the following steps:
melting a wax;
adding to the melted wax, an oil, an emulsifier, a preservative, and water heated above the melting temperature of the wax to form the wax emulsion; and
cooling the wax emulsion.

18. The method of claim 17, wherein the wax is either paraffin wax or microcrystalline wax, the oil is soy oil, the emulsifier is sorbitan monostearate and the preservative is vitamin E.

* * * * *